United States Patent
Murakita et al.

(10) Patent No.: US 10,028,647 B2
(45) Date of Patent: Jul. 24, 2018

(54) MEDICAL OBSERVATION DEVICE AND MEDICAL OBSERVATION METHOD

(71) Applicants: SONY CORPORATION, Tokyo (JP); SONY OLYMPUS MEDICAL SOLUTIONS INC., Hachioji-shi (JP)

(72) Inventors: Masashi Murakita, Chiba (JP); Takahiro Yamamoto, Tokyo (JP)

(73) Assignees: SONY CORPORATIONS, Tokyo (JP); SONY OLYMPUS MEDICAL SOLUTIONS INC., Hachioji-shi (JP)

( * ) Notice: Subject to any disclaimer, the term of this patent is extended or adjusted under 35 U.S.C. 154(b) by 0 days.

(21) Appl. No.: 15/323,742

(22) PCT Filed: May 12, 2016

(86) PCT No.: PCT/JP2016/064125
§ 371 (c)(1),
(2) Date: Jan. 4, 2017

(87) PCT Pub. No.: WO2017/010156
PCT Pub. Date: Jan. 19, 2017

(65) Prior Publication Data
US 2017/0196443 A1 Jul. 13, 2017

(30) Foreign Application Priority Data

Jul. 13, 2015 (JP) ................................. 2015-139312

(51) Int. Cl.
*A61B 1/00* (2006.01)
*A61B 1/045* (2006.01)
(Continued)

(52) U.S. Cl.
CPC .............. *A61B 1/045* (2013.01); *A61B 1/051* (2013.01); *G02B 21/365* (2013.01);
(Continued)

(58) Field of Classification Search
CPC ....... A61B 1/045; G02B 21/365; H04N 5/2256
(Continued)

(56) References Cited

U.S. PATENT DOCUMENTS 6,836,288 B1  12/2004  Lewis
7,653,300 B2 *  1/2010  Fujiyoshi ............. G02B 21/367
                                                          348/79
(Continued)

FOREIGN PATENT DOCUMENTS

CN        1849817 A    10/2006
EP     2 081 072 A1     7/2009
(Continued)

OTHER PUBLICATIONS

International Search Report dated Aug. 2, 2016 in PCT/JP2016/064125 filed May 12, 2016 (Translation of Category of Cited Documents in attached foreign language Search Report).

(Continued)

*Primary Examiner* — Jeffery Williams
(74) *Attorney, Agent, or Firm* — Oblon, McClelland, Maier & Neustadt, L.L.P.

(57) ABSTRACT

[Object] To suppress sudden changes in brightness due to a disturbance in a captured image.
[Solution] Provided is a medical observation device, including: an acquisition section that acquires a sensing result of a brightness of an image of a subject in a living organism; and a control section that decides, according to a first interval in which the brightness sensing result indicates a value inside a certain range, a second interval in which to maintain an exposure of an imaging section at an exposure corresponding to a value included in the range.

12 Claims, 10 Drawing Sheets

(51) Int. Cl.
*A61B 1/05* (2006.01)
*H04N 5/235* (2006.01)
*H04N 5/225* (2006.01)
*G02B 23/24* (2006.01)
*G02B 21/36* (2006.01)

(52) U.S. Cl.
CPC ....... *G02B 23/2484* (2013.01); *H04N 5/2256* (2013.01); *H04N 5/2351* (2013.01); *H04N 2005/2255* (2013.01)

(58) Field of Classification Search
USPC .......................................................... 348/68
See application file for complete search history.

(56) References Cited

U.S. PATENT DOCUMENTS

| | | |
|---|---|---|
| 2002/0191086 A1 | 12/2002 | Masuyama |
| 2006/0210262 A1 | 9/2006 | Fujiyoshi et al. |
| 2007/0024741 A1* | 2/2007 | Moriya ................ H04N 5/2352 348/363 |
| 2014/0046341 A1 | 2/2014 | DiCarlo |
| 2015/0373246 A1* | 12/2015 | Arakawa .............. H04N 5/2356 348/234 |

FOREIGN PATENT DOCUMENTS

| | | |
|---|---|---|
| JP | 10-333204 A | 12/1998 |
| JP | 2000-152913 A | 6/2000 |
| JP | 2001-37711 A | 2/2001 |
| JP | 2004-321413 A | 11/2004 |
| JP | 4187578 | 9/2008 |

OTHER PUBLICATIONS

Written Opinion dated Aug. 2, 2016 in PCT/JP2016/064125 filed May 12, 2016.
Office Action dated Jan. 31, 2017 in Japanese Patent Application No. 2016-558152.
Search Report dated Oct. 30, 2017, in Europe Patent Application No. 16816567.8-1666 / 3158917 PCT/JP2016064125. (9 pages).
Office Action dated Jan. 29, 2018, in Chinese Patent Application No. 2016800019772 with English-language translation.

* cited by examiner

MEDICAL OBSERVATION DEVICE AND MEDICAL OBSERVATION METHOD

TECHNICAL FIELD

The present disclosure relates to a medical observation device and a medical observation method.

BACKGROUND ART

Recently, due to advancements in surgical techniques and surgical equipment, surgeries for performing various treatments (also called microsurgery) while observing an affected site with an observation device for medical use, such as an endoscope or a surgical microscope, are coming to be conducted frequently. Also, such observation devices for medical use are not limited to devices that enable optical observation of the affected area, and also include devices that display an image of the affected area captured by an imaging section (camera) or the like as an electronic image on a display such as a monitor. For example, Patent Literature 1 discloses an example of a technology that captures an observation image from an endoscope with an imaging section, and displays the captured observation image as an electronic image on a display.

CITATION LIST

Patent Literature

Patent Literature 1: JP 2001-37711A

DISCLOSURE OF INVENTION

Technical Problem

On the other hand, for example, under circumstances in which a medical observation device such as an endoscope or a surgical microscope is used, a case is conceivable in which objects such as forceps and gauze are inserted into the observation range of the medical observation device (that is, inside the field of view of the imaging section). In this way, under circumstances in which a comparatively brighter object than the target of observation (in other words, a high-luminance subject) enters into the field of view of the imaging section, in some cases the brightness in the field of view may be treated as having become brighter, and an action such as controlling the shutter speed more rapidly or decreasing the gain may be performed to control the exposure (amount of exposure) of the imaging section so that the captured image of the subject becomes darker, for example. Such cases may sometimes reveal a phenomenon in which the brightness of the image changes suddenly, such as the output image of the target of observation (in other words, the image of the subject) becoming dark temporarily, for example. Such brightness changes in the image (particularly, the image of the target of observation) due to an outside disturbance may be anticipated to obstruct the work of the surgeon performing a medical procedure while observing the image.

Accordingly, the present disclosure proposes a medical observation device and a medical observation method capable of suppressing sudden changes in brightness due to a disturbance in a captured image.

Solution to Problem

According to the present disclosure, there is provided a medical observation device, including: an acquisition section that acquires a sensing result of a brightness of an image of a subject in a living organism; and a control section that decides, according to a first interval in which the brightness sensing result indicates a value inside a certain range, a second interval in which to maintain an exposure of an imaging section at an exposure corresponding to a value included in the range.

According to the present disclosure, there is provided a medical observation method, executed by a processor, including: acquiring a sensing result of a brightness of an image of a subject in a living organism; and deciding, according to a first interval in which the brightness sensing result indicates a value inside a certain range, a second interval in which to maintain an exposure of an imaging section at an exposure corresponding to a value included in the range.

Advantageous Effects of Invention

According to the present disclosure as described above, there is provided a medical observation device and a medical observation method capable of suppressing sudden changes in brightness due to a disturbance in a captured image.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
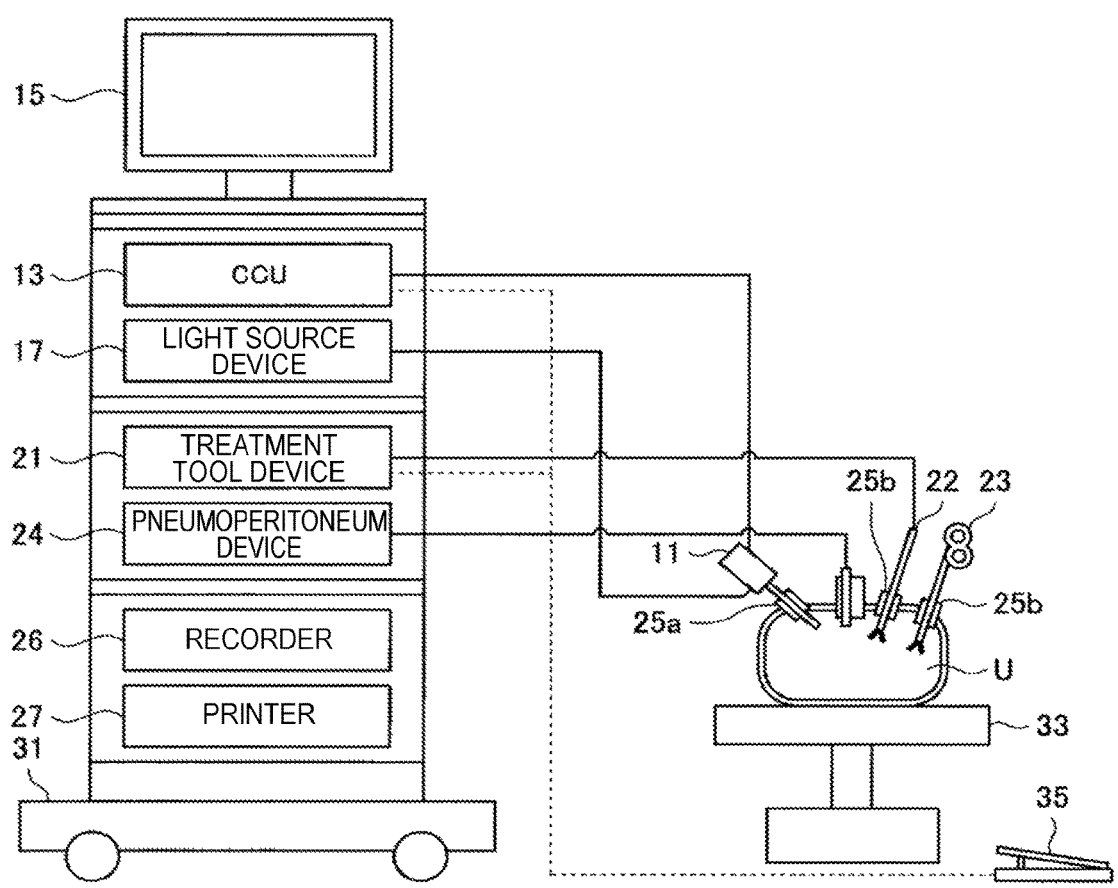
FIG. 1 is an explanatory diagram for explaining an example of a schematic configuration of a system applying a medical observation device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. System configuration
2. Investigation regarding exposure control
3. Functional configuration
4. Processes
5. Modifications
6. Applications
7. Hardware configuration
8. Conclusion <1. System Configuration>

First, an example of the configuration of a system applying a medical observation device according to the present embodiment will be described with reference to FIG. 1. FIG. 1 is an explanatory diagram for explaining an example of a schematic configuration of a system applying a medical observation device according to the present embodiment.

For example, FIG. 1 illustrates an example of an endoscopic surgical system used in endoscopic surgeries of the abdomen, conducted as a substitute for abdominal surgeries of the past in the medical field. As illustrated in FIG. 1, in an endoscopic surgery of the abdomen, instead of opening up the abdomen by cutting abdominal wall like in the past, hole-opening tools called trocars 25*a* and 25*b* are attached to the abdominal wall in several places, and tools such as a laparoscope (hereinafter also called an endoscope) 11, an energy treatment tool 22, and forceps 23 are inserted into the body through holes provided in the trocars 25*a* and 25*b*. Subsequently, a treatment such as excising an affected area U is conducted with the energy treatment tool 22 and the like while viewing in real-time an image of the affected area (such as a tumor) U video-captured by the endoscope 11. Note that the endoscope 11, the energy treatment tool 22, and the forceps 23 are held by a surgeon, an assistant, a scopist, or a robot or the like.

Inside the operating room where such an endoscopic surgery takes place, a cart 31 bearing devices for the endoscopic surgery, a patient bed 33 on which the patient lies, a footswitch 35, and the like are disposed. Also, on the cart 31, devices such as a camera control unit (CCU) 13, a light source device 17, a treatment tool device 21, a pneumoperitoneum device 24, a display device 15, a recorder 26, and a printer 27 are placed as medical equipment.

An image signal of the affected area U captured through an observation optical system of the endoscope 11 is transmitted to the CCU 13 via a camera cable. Note that the CCU 13, besides being connected to the endoscope 11 via the camera cable, may also be connected to the endoscope 11 via a wireless communication link. The CCU 13 performs signal processing on the image signal output from the endoscope 11, and outputs the processed image signal to the display device 15. According to such a configuration, an endoscopic image of the affected area U is displayed on the display device 15.

Note that the CCU 13 may also output the processed image signal to the recorder 26, and thereby cause the recorder 26 to record the endoscopic image of the affected area U as image data (for example, moving image data). Additionally, the CCU 13 may also output the processed image signal to the printer 27, and thereby cause the printer 27 to print out an endoscopic image of the affected area U.

The light source device 17 is connected to the endoscope 11 via a light guide cable, and is able to radiate light onto the affected area U while switching among various wavelengths of light. Note that in some cases, the light radiated from the light source device 17 is also used as auxiliary light, for example.

The treatment tool device 21 corresponds to a high-frequency output device that outputs a high-frequency current to the energy treatment tool 22 that cuts the affected area U using electrical heat, for example.

Additionally, the pneumoperitoneum device 24 is provided with blowing and suction means, and is for blowing air into the patient's body cavity, such as the abdominal region, for example.

The footswitch 35 is configured to control the CCU 13, the treatment tool device 21, or the like by using a foot operation by a person such as the surgeon or an assistant as a trigger signal.

The above thus references FIG. 1 to describe an example of a schematic system configuration of what may be termed an endoscopic surgical system 1 as a system configuration applying a medical observation device according to an embodiment of the present disclosure.

<2. Investigation Regarding Exposure Control>

Next, to more easily understand the features of a medical observation device according to an embodiment of the present disclosure, an overview of exposure control in an imaging section included in the endoscope 11 or the like will be described, followed by a summary of the challenges of a medical observation device according to the present embodiment.

The imaging section is sometimes configured so that exposure is controlled according to a sensing result of the brightness of a subject image or the brightness of a captured image of the subject (in other words, configured so that the brightness of the captured image of the subject is controlled). Note that in the present description, for the sake of convenience, the primary agent that controls the exposure of the imaging section is described as being the CCU.

For example, the CCU senses (detects) the brightness of a subjected captured in an image (image plane luminous intensity), based on an image signal captured by an image sensor such as a complementary metal-oxide-semiconductor (CMOS) image sensor or a charge-coupled device (CCD) image sensor (for example, an image sensor provided in the imaging section). Also, as another example, the CCU may also acquire a sensing result of the brightness (illuminance) of a subject image from a sensing section such as a photometric sensor provided in the imaging section. Note that in the following description, the detection result for the brightness of a subject image or the brightness of a captured image of a subject may sometimes be designated simply the "detection value". Subsequently, the CCU, based on the acquired detection value, controls the shutter speed of the imaging section or controls the gain applied to the captured image signal (in other words, controls the exposure of the imaging section) so that the brightness of the image of the subject captured by the imaging section (that is, the image plane luminous intensity) becomes a more preferable state (for example, to reach a correct exposure). Note that in the following description, the term "gain", unless specifically noted otherwise, refers to the gain applied to a captured image signal.

Figure 2:
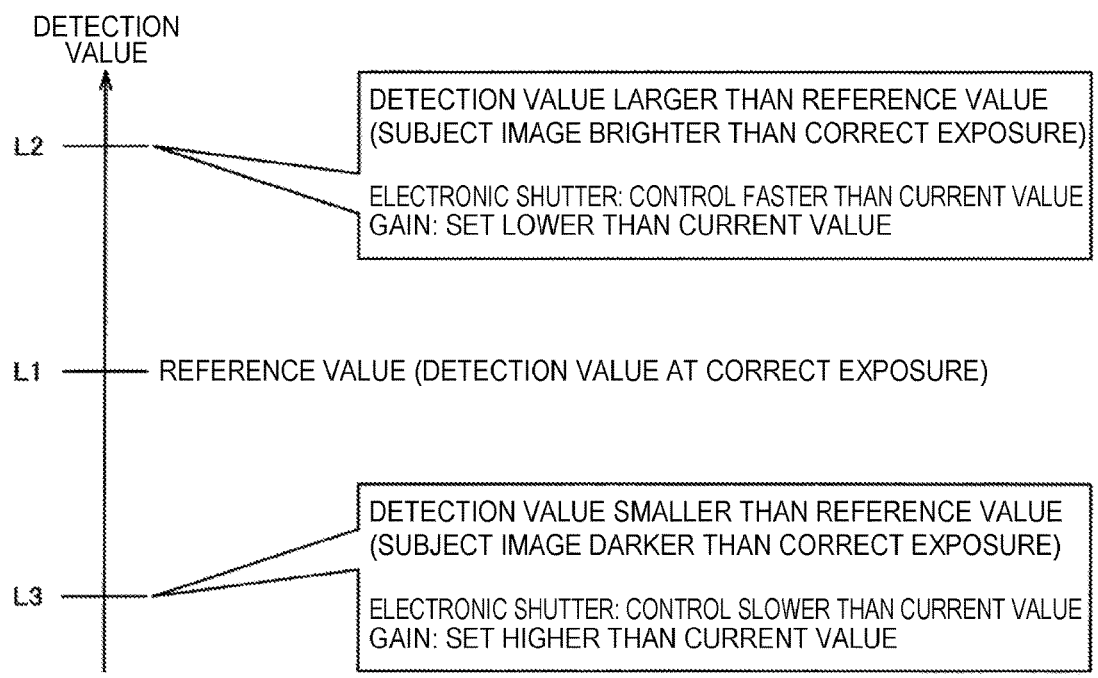
FIG. 2 is an explanatory diagram for explaining an example of exposure control.

For example, FIG. 2 is an explanatory diagram for explaining an example of exposure control. In FIG. 2, the reference sign L1 indicates the detection value in the case in which the brightness of the captured image of the subject is correct (that is, the detection value at which a correct exposure is reached). Note that in the following, the detection value indicated by the reference sign L1 may sometimes be designated the "reference value".

In contrast, the reference sign L2 indicates a detection value greater than the reference value L1. In other words, if the detection value L2 is acquired, the brightness of the image of the subject is brighter than the case of a correct exposure. For this reason, in this case, the CCU controls the exposure of the imaging section to decrease the amount of exposure. Specifically, the CCU controls the shutter speed of an electronic shutter of the imaging section to be faster than the current value, for example. Additionally, the CCU may also control the gain to be lower than the current value. According to such control, the captured image of the subject is controlled to become darker, or in other words, the brightness of the image is controlled to approach the brightness of an image corresponding to the reference value L1.

In addition, the reference sign L3 indicates a detection value smaller than the reference value L1. In other words, if the detection value L3 is acquired, the brightness of the image of the subject is darker than the case of a correct exposure. For this reason, in this case, the CCU controls the exposure of the imaging section to increase the amount of exposure. Specifically, the CCU controls the shutter speed of an electronic shutter of the imaging section to be slower than the current value, for example. Additionally, the CCU may also control the gain to be higher than the current value. According to such control, the captured image of the subject is controlled to become brighter, or in other words, the brightness of the image is controlled to approach the brightness of an image corresponding to the reference value L1.

On the other hand, as discussed earlier with reference to FIG. 1, under circumstances in which a medical observation device is used, such as during an endoscopic surgery of abdomen, a case is conceivable in which objects different from the target of observation (test subject), such as forceps and gauze, are inserted into the observation range of the medical observation device (that is, inside the field of view of the imaging section). Particularly, under circumstances in which a comparatively brighter object than the target of observation (in other words, a high-luminance subject) enters into the field of view of the imaging section, in some cases the brightness in the field of view may be treated as having become brighter, and an action of controlling the exposure of the imaging section (for example, controlling the shutter speed more rapidly or decreasing the gain) may be performed so that the captured image of the subject becomes darker. Such cases may sometimes reveal a phenomenon in which the brightness of the image of the subject changes suddenly, such as the output image of the target of observation (for example, the image of the affected area inside the body) becoming dark temporarily, for example. Such brightness changes in the image (particularly, the image of the target of observation, such as the affected area) due to an outside disturbance may be anticipated to obstruct the work of the surgeon performing a medical procedure while observing the image.

Accordingly, a medical observation device according to the present embodiment provides a mechanism enabling the suppression of sudden changes in the brightness of the captured image, even under circumstances in which a disturbance occurs, such as a high-luminance subject, like forceps or gauze, entering into the observation range. Note that in the following, a medical observation device according to the present embodiment will be described in further detail.

<3. Functional Configuration>

Figure 3:
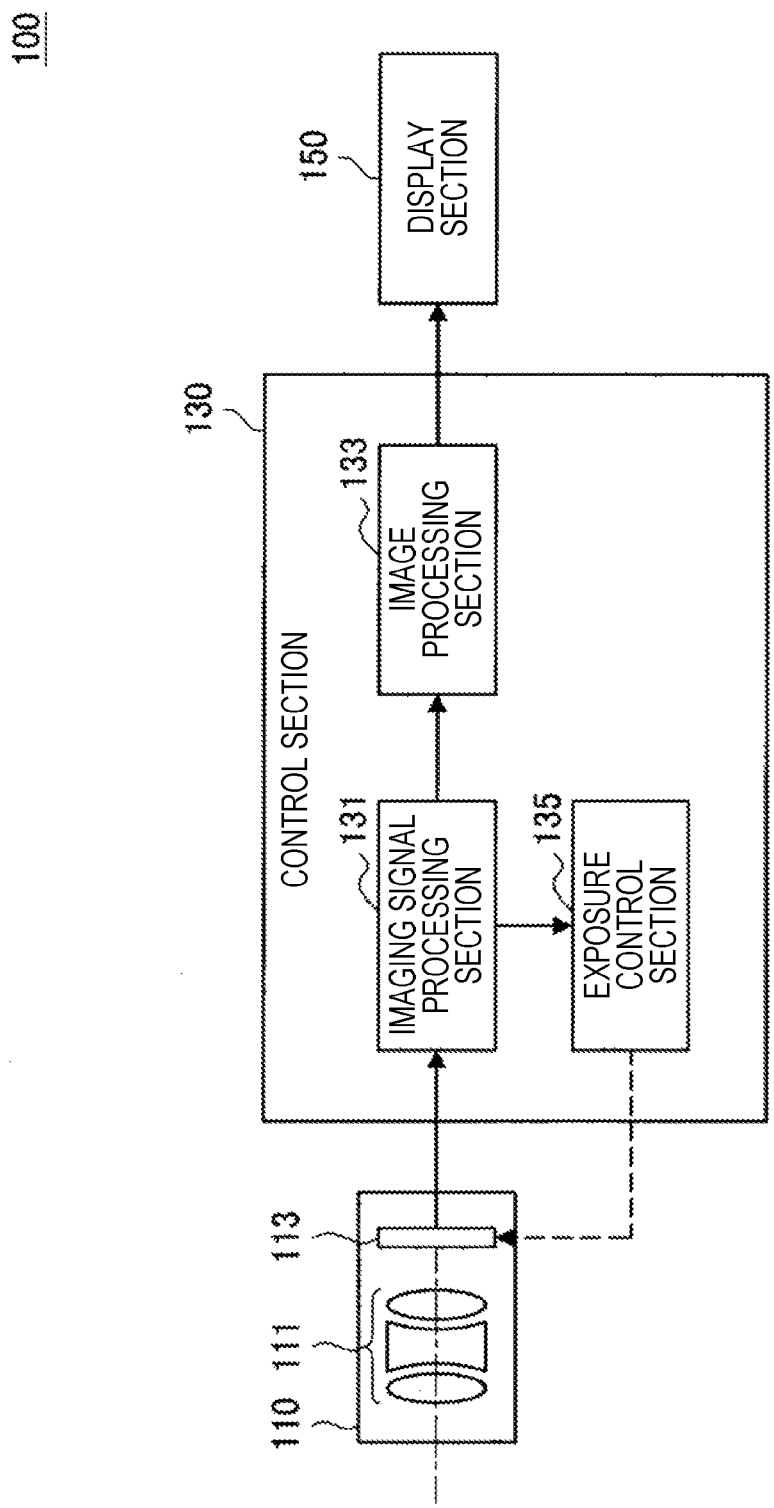
FIG. 3 is a block diagram illustrating an example of a functional configuration of a medical observation device according to the embodiment.

First, FIG. 3 will be referenced to describe an example of a functional configuration of a medical observation device according to the present embodiment, with particular focus on operations related to the control of the brightness of a captured image of a subject (in other words, exposure control). FIG. 3 is a block diagram illustrating an example of a functional configuration of a medical observation device according to the present embodiment, and illustrates an example of a functional configuration with particular focus on a process of capturing an image of a target of observation (test subject) and displaying the image.

As illustrated in FIG. 3, a medical observation device 100 according to the present embodiment includes an imaging section 110 (for example, a camera head), a control section 130, and a display section 150. Note that the medical observation device 100 illustrated in FIG. 3 may be configured as the endoscopic system 1 illustrated in FIG. 1, for example. In other words, the imaging section 110, the control section 130, and the display section 150 illustrated in FIG. 3 correspond respectively to the endoscope 11, the CCU 13, and the display device 15 in the endoscopic surgical system 1 illustrated in FIG. 1, for example.

The imaging section 110 corresponds to a configuration that captures an image such as a moving image or a still image, like what is commonly called a camera or the like, and includes an imaging optical system (for example, a series of lens groups) 111, and an image sensor 113. The imaging optical system 111 focuses an optical image of a subject on the imaging surface of the image sensor 113. For the image sensor 113, a sensor such as a CMOS image sensor or a CCD image sensor may be applied, for example. The image sensor 113 converts the optical image focused on the imaging surface into an electrical signal by photoelectric conversion. Note that the operation of the image sensor 113 at this point (for example, the shutter speed or gain) is controlled by the control section 130 discussed later (in other words, exposure is controlled by the control section 130). Subsequently, the image sensor 113 outputs the electrical signal generated by photoelectric conversion to the control section 130.

The control section 130 includes an imaging signal processing section 131, an image processing section 133, and an exposure control section 135.

The imaging signal processing section 131 generates an image signal by executing various processes on the electrical signal generated by photoelectric conversion in the image sensor 113, such as a linear matrix process, a white balance process, and a gamma correction process, for example. The image signal generated by the imaging signal processing section 131 is input into the image processing section 133. The image processing section 133 performs image processing on the acquired image signal depending on the intended purpose, such as various correction processes like color correction and luminance correction, video signal generation, or an encoding process or the like, and outputs an image based on the result of the image processing to the display section 150, for example.

In addition, the imaging signal processing section 131 outputs information required for exposure control of the image sensor 113 to the exposure control section 135. More specifically, the imaging signal processing section 131 performs detection processing on the electrical signal generated by photoelectric conversion in the image sensor 113, and outputs a result of the detection process (namely, a detection value) to the exposure control section 135.

The exposure control section 135 acquires a detection value as a result of the detection processing from the imaging signal processing section 131, and based on the acquire detection value, controls the shutter speed or the gain of the image sensor 113 (in other words, controls the exposure of the imaging section 110). For example, as discussed earlier with reference to FIG. 2, if the acquired detection value is divergent from a reference value, the exposure control section 135 may treat the reference value as a target value, and control the exposure of the imaging section 110 so that the acquired detection value approaches the target value.

As a more specific example, if the brightness of the image of the subject based on the detection value is recognized to be brighter than the case of a correct exposure corresponding to the reference value, the exposure control section 135 controls the exposure of the imaging section 110 so that the amount of exposure becomes smaller. In this case, for example, the exposure control section 135 controls the shutter speed of an electronic shutter in the image sensor 113 more rapidly, or controls the gain to be lower.

Also, as another example, if the brightness of the image of the subject based on the detection value is recognized to be darker than the case of a correct exposure corresponding to the reference value, the exposure control section 135 controls the exposure of the imaging section 110 so that the amount of exposure becomes larger. In this case, for example, the exposure control section 135 controls the shutter speed of an electronic shutter in the image sensor 113 more slowly, or controls the gain to be higher.

In addition, if the detection value indicates a value inside a certain range, the exposure control section 135, by exposure control subjected to a disturbance such as a high-luminance subject entering into the observation range, suppresses sudden changes in exposure in order to suppress the occurrence of a situation in which the brightness of the image of the subject changes suddenly.

Specifically, in the case of recognizing that the detection value indicates a value inside a certain range, the exposure control section 135 measures a first interval in which the detection value indicates a value inside the range, and based on the measurement result of the first interval, decides a second interval in which to suppress sudden changes in exposure due to a disturbance. Note that the certain range (that is, the range of the detection value) is decided in advance, based on a range of allowed exposure (in other words, the preferred brightness of the image of the subject for observation of the target), using the detection value corresponding to a correct exposure as a reference, for example.

Subsequently, even if the detection value changes suddenly due to a disturbance or the like during the decided second interval, the exposure control section 135 controls the operation of the image sensor 113 so that an exposure corresponding to a detection value inside the certain range (for example, the correct exposure corresponding to the reference value) is maintained. Note that the details of this operation will be discussed separately later, together with an example of the flow of a series of processes by the medical observation device.

The above thus references FIG. 3 to describe an example of a functional configuration of a medical observation device according to the present embodiment, with particular focus on operations related to the control of the brightness of an image of a subject (in other words, exposure control).

<4. Processes>

Figure 4:
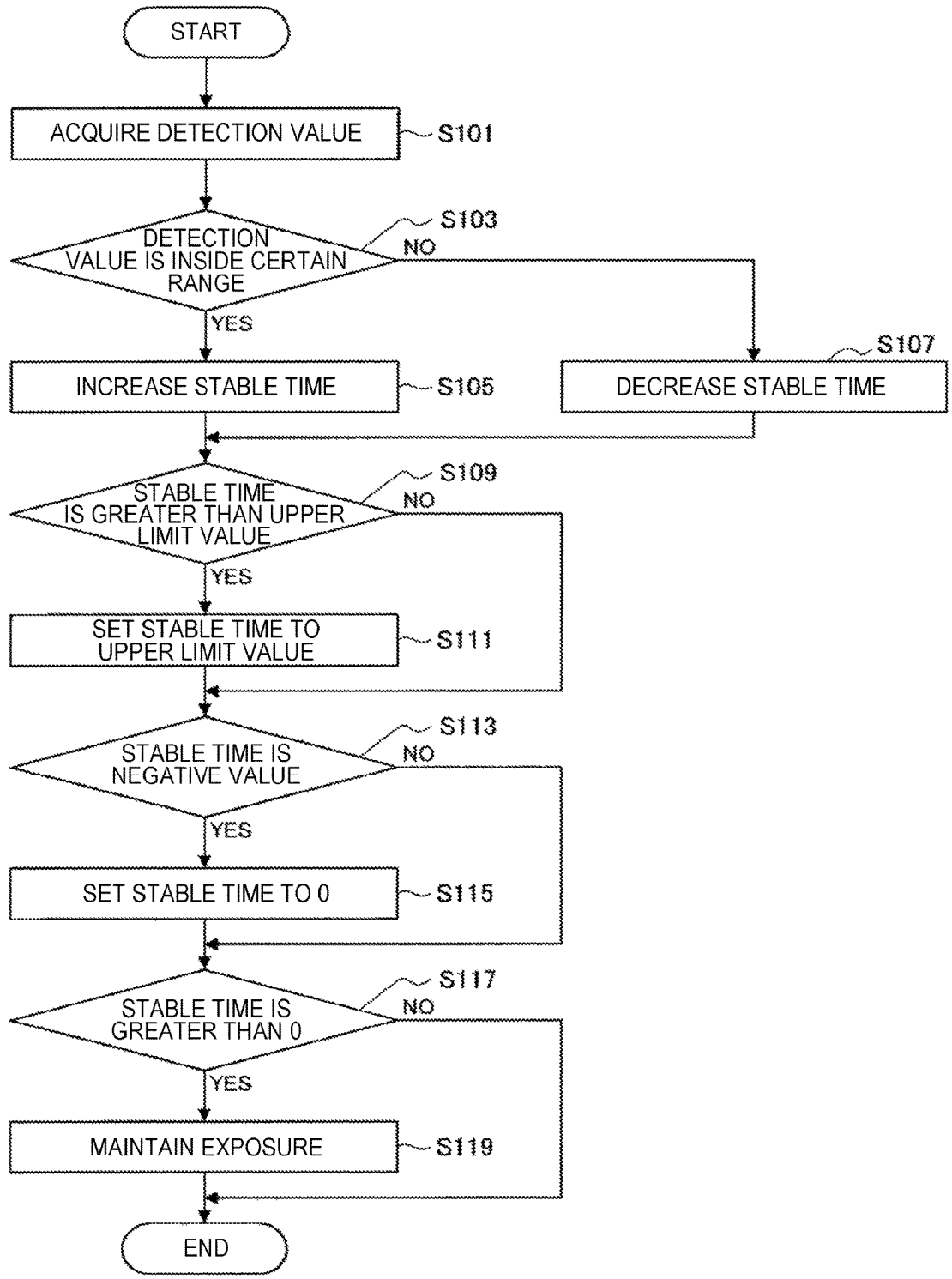
FIG. 4 is a flowchart illustrating an example of the flow of a series of processes by a medical observation device according to the embodiment.

Next, FIG. 4 will be referenced to describe an example of the flow of a series of processes by the medical observation device according to the present embodiment, with particular focus on the operation of exposure control by the medical observation device. FIG. 4 is a flowchart illustrating an example of the flow of a series of processes by the medical observation device according to the present embodiment.

(Step S101)

First, the imaging signal processing section 131 performs detection processing on the electrical signal generated by photoelectric conversion in the image sensor 113, and outputs a result of the detection process (namely, a detection value) to the exposure control section 135.

(Step S105)

If the detection value acquired from the imaging signal processing section 131 indicates a value inside a certain range, the exposure control section 135 increases an interval over which to maintain exposure (hereinafter designated the "stable time Ts") even if the detection value changes suddenly due to a disturbance or the like. Note that in the present description, the stable time Ts is described as being managed based on a counter value that counts one frame as 1. In other words, in this case, the exposure control section 135 increments the counter value of the stable time Ts.

(Step S107)

In addition, if the acquired detection value indicates a value outside the certain range, the exposure control section 135 decrements the counter value of the stable time Ts. In other words, in this case, the stable time Ts is decreased.

(Steps S109, S111)

Note that an upper limit value on the stable time Ts may also be provided. In such a case, when the counter value of the stable time Ts is greater than the upper limit value (S109, YES), the exposure control section 135 may set the counter value of the stable time Ts to the upper limit value (S111). Such control thereby deters a situation in which the stable time Ts is increased past the upper limit value. Note that if the counter value of the stable time Ts is less than or equal to the upper limit value (S109, NO), the flow proceeds to the next process, without executing the process indicated by the reference sign S111.

(Steps S113, S115)

In addition, if the counter value of the stable time Ts indicates a negative value (S113, YES), the exposure control section 135 sets the counter value of the stable time Ts to 0. Such control thereby deters a situation in which the stable time Ts is decreased past 0. Note that if the counter value of the stable time Ts is equal to or greater than 0 (S113, NO), the flow proceeds to the next process, without executing the process indicated by the reference sign S115.

(Steps S117, S119)

In addition, if the counter value of the stable time Ts is greater than 0 (S117, YES), the exposure control section 135 treats the detection value inside the certain range discussed above (in other words, the detection value range) as a target value, and controls the operation of the imaging section 110 so that the exposure of the imaging section 110 is maintained at an exposure corresponding to the target value. As a more specific example, at this point the exposure control section 135 locks the shutter speed of the electronic shutter in the image sensor 113 or the gain so that the exposure of the imaging section 110 is maintained at a correct exposure corresponding to the reference value (S119). Note that if the counter value of the stable time Ts is not greater than 0 (in other words, in the case of 0) (S117, NO), the exposure control section 135 does not execute the control related to maintaining exposure indicated by the reference sign S119.

In this case, for example, the exposure control section 135 controls the exposure of the imaging section 110 according to the acquired detection value so that the detection value approaches the target value (reference value).

Figure 5:
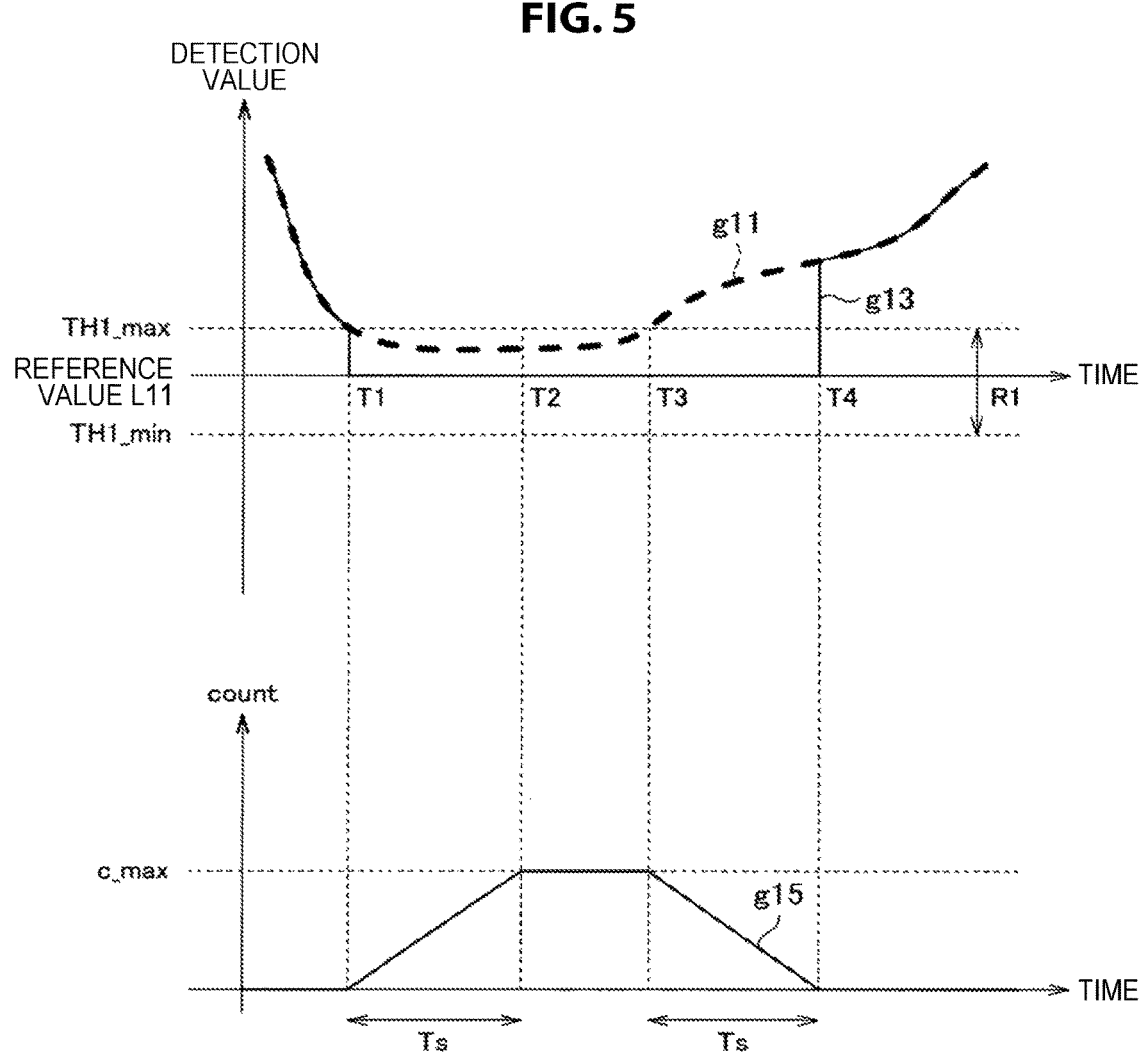
FIG. 5 is an explanatory diagram for explaining an example of exposure control by a medical observation device according to the embodiment.

The medical observation device 100 according to the present embodiment successively executes a series of operations as described above at every instance of a certain timing, for example. Accordingly, next, an example of exposure control based on the series of operations discussed above by a medical observation device according to the present embodiment will be described with reference to FIG. 5. FIG. 5 is an explanatory diagram for explaining an example of exposure control by a medical observation device according to the present embodiment, and illustrates an example of the relationship among the detection value, the exposure control, and the counter value for managing the stable time. In FIG. 5, the horizontal axis of the graph illustrated on the top and the graph illustrated on the bottom represents time. Also, the vertical axis of the graph illustrated on the top represents the detection value. Also, the vertical axis of the graph illustrated on the bottom illustrates the counter value of the stable time.

In addition, in FIG. 5, the graph indicated by the reference sign g11 represents the chronological change in the detection value acquired based on the detection process by the imaging signal processing section 131. Also, the graph indicated by the reference sign g13 illustrates the chronological change in the exposure based on the control by the exposure control section 135 diagrammatically as the chronological change in the detection value corresponding to the exposure. Also, the graph indicated by the reference sign g15 represents the chronological change in the counter value of the stable time.

Also, the reference sign R1 indicates the certain range discussed earlier (in other words, the detection value range). Note that in the example illustrated in FIG. 5, a range of ±TH1 centered on a reference value L11 is set as the certain range R1 Herein, the reference sign TH1_max indicates a threshold value on the + side of the certain range R1 (that is, an upper limit value), while the reference sign TH1_min indicates a threshold value on the − side of the certain range R1 (that is, a lower limit value). In such a case, when the absolute value of the difference between the acquired detection value and the reference value L11 is less than or equal to the threshold value TH1, it is possible to recognize that the detection value indicates a value inside the certain range R1. Note that the method of setting the certain range R1 (in other words, the detection value range) described above is merely one example, and it is not necessarily required to set a range centered on a reference value.

In the example illustrated in FIG. 5, as illustrated by the graph g11, the acquired detection value indicates a value inside the certain range R1 in the interval from the timings T1 to T3, and indicates a value outside the certain range R1 from the timing T3.

At this point, consider the chronological change in the counter value of the stable time illustrated as the graph g15. Since the detection value indicates a value inside the range R1 in the interval from the timings T1 to T2, the counter value of the stable time increases chronologically, and reaches an upper limit c_max of the counter value at the timing T2. Also, in the interval from the timings T2 to T3, the detection value indicates a value inside the range R1, but the counter value of the stable time has reached the upper limit c_max, and thus is maintained so as not to exceed the upper limit c_max. Also, from the timing T3, the detection value indicates a value outside the range R1, and thus the counter value of the stable time decreases chronologically by the amount the counter value increased in the interval from the timings T1 to T2, and becomes 0 at the timing T4. In other words, in the example illustrated in FIG. 5, the counter value that increased over the time Ts of length from the timings T2 to T2 decreases over the stable time Ts, and reaches 0.

Next, the exposure control of the imaging section 110 by the exposure control section 135 will be described with reference to the graph g13. In the example illustrated in FIG. 5, if the counter value of the stable time is indicating a value greater than 0, the exposure control section 135 treats the reference value L11 (in other words, a detection value inside the range R1) as a target value, and controls the operation of the imaging section 110 so that the exposure of the imaging section 110 is maintained at an exposure corresponding to the target value (in other words, the correct exposure corresponding to the reference value L11).

More specifically, in the example illustrated in FIG. 5, in the interval from the timings T1 to T4, the counter value of the stable time indicates a value greater than 0. For this reason, in this interval, the exposure control section 135 controls the operation of the imaging section 110 so that the exposure of the imaging section 110 is maintained at the correct exposure corresponding to the reference value L11.

At this point, consider the interval from the timing T3. As discussed above, from the timing T3, the detection value rises due to a disturbance, such as a high-luminance subject entering into the observation range, for example, and the detection value indicates a value outside the range R1. Meanwhile, in the interval also from the timing T3 until the timing T4 at which the counter value of the stable time decreases to reach 0, the exposure control section 135 maintains the exposure of the imaging section 110 at the correct exposure corresponding to the reference value L11, and from the timing T4, switches to exposure control that follows the detection value.

According to such control, even when the detection value changes suddenly due to a disturbance, like a high-luminance subject such as forceps or gauze entering into the observation range, the medical observation device 100 maintains the exposure of the imaging section 110, and suppresses sudden changes of brightness in the image of the subject (image of the target of observation). In other words, according to the medical observation device 100 according to the present embodiment, even when a disturbance occurs, like a high-luminance object such as forceps or gauze temporarily entering into the observation range, it becomes possible to suppress the occurrence of a situation in which the captured image of the target of observation becomes dark.

Additionally, even when the detection value indicates a value outside the range R1, the interval in which the medical observation device 100 maintains the exposure of the imaging section 110 at the correct exposure (second interval) is decided according to the interval in which the acquired detection value indicates a value inside the certain range R1 (first interval). More specifically, the medical observation device 100 performs control so that as the interval in which the detection value indicates a value inside the certain range R1 (first interval) becomes longer, the interval in which the exposure of the imaging section 110 is maintained at the correct exposure even if the detection value indicates a value outside the range R1 (second interval) also becomes longer.

For example, in the example illustrated in FIG. 5, the interval from the timings T1 to T3 corresponds to the interval in which the detection value indicates a value inside the certain range R1 (first interval). Also, the interval from the timings T1 to T4 corresponds to the interval in which the exposure of the imaging section 110 is maintained at the correct exposure (second interval). In other words, the medical observation device 100 according to the present embodiment dynamically controls the interval in which the exposure of the imaging section 110 is maintained at the correct exposure, according to changes of brightness in the observation range. For this reason, according to the medical observation device 100 according to the present embodiment, it becomes possible to achieve, with a more favorable mode, both the suppression of sudden changes of brightness in the image of the subject as discussed above, and the tracking of the brightness of the image with respect to changes of brightness in the observation range.

The foregoing thus references FIGS. 4 and 5 to describe an example of the flow of a series of processes by the medical observation device according to the present embodiment, with particular focus on the operation of exposure control by the medical observation device.

<5. Modifications>

Next, as a modification of the medical observation device according to the present embodiment, another example of exposure control by the medical observation device will be described. As discussed above, the medical observation device according to the present embodiment calculates a second interval in which to suppress sudden changes in exposure due to a disturbance, based on a first interval in which the detection value indicates a value inside the certain range R1. On the other hand, the mode of such control is not particularly limited, insofar as the medical observation device is able to maintain the exposure of the imaging section 110 at an exposure based on a detection value inside the range R1 in the second interval.

For example, in the example discussed above with reference to FIG. 5, the medical observation device 100 starts the control of the imaging section 110 so that the exposure of the imaging section 110 reaches the correct exposure, while using the timing T1 at which the acquired detection value indicates a value inside the certain range R1 as a base point. On the other hand, insofar as the exposure of the imaging section 110 is maintained at an exposure based on a detection value inside the certain range R1 in the interval from the timings T1 to T4, the timing at which the medical observation device 100 starts the control of the operation of the imaging section 110 is not necessarily limited to the timing T1 in FIG. 5.

Figure 6:
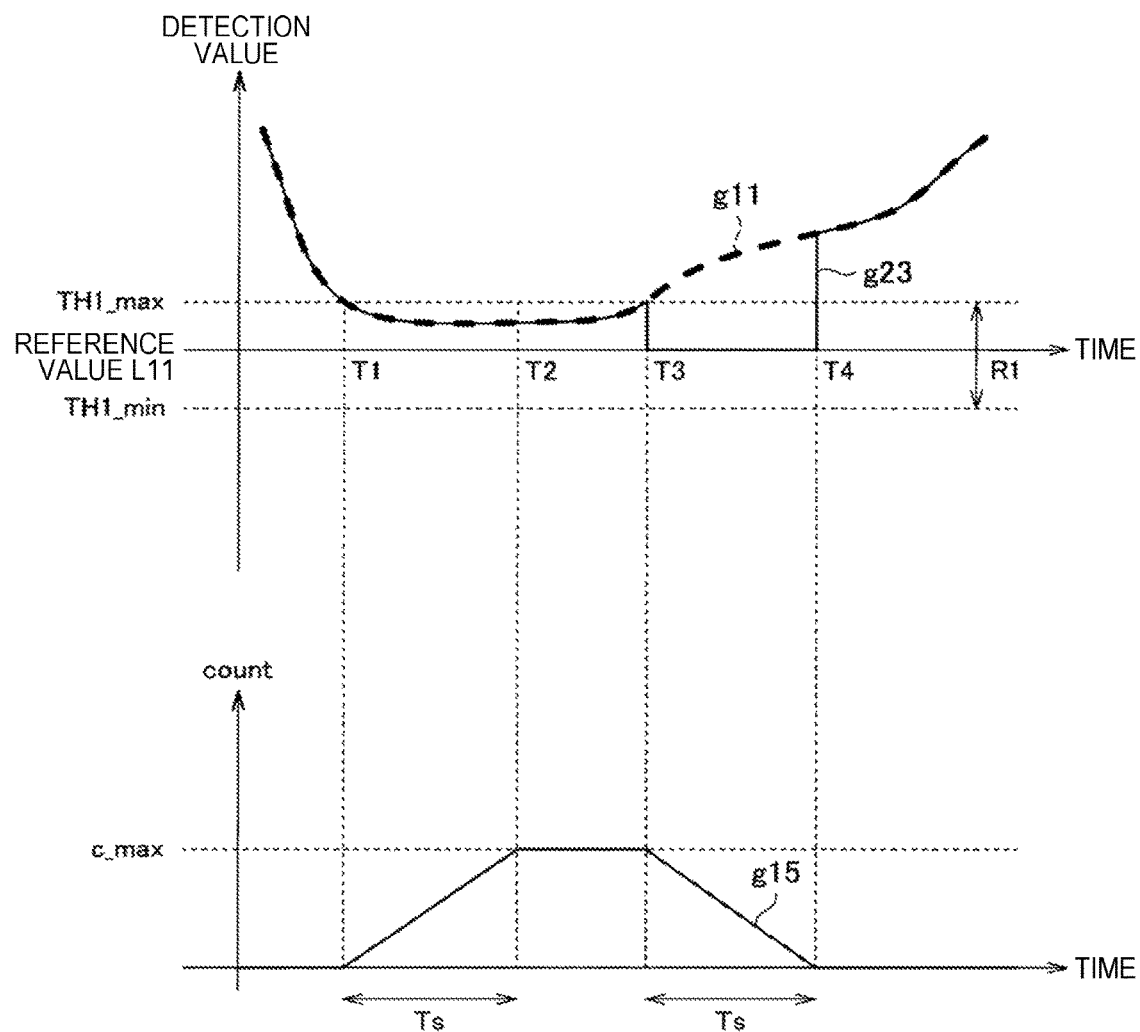
FIG. 6 is an explanatory diagram for explaining an example of exposure control by a medical observation device according to a modification of the embodiment.

For example, FIG. 6 is an explanatory diagram for explaining an example of exposure control by a medical observation device according to a modification of the present embodiment. Also, the vertical axis and the horizontal axis in each of the graphs respectively illustrated on the top and the bottom of FIG. 6 correspond to the vertical axis and the horizontal axis of the graphs respectively illustrated on the top and the bottom of FIG. 5. Note that in the example illustrated in FIG. 6, the graphs indicated by the reference signs g11 and g15 are similar to the graphs g11 and g15 in the example illustrated in FIG. 5, and thus detailed description will be reduced or omitted. Also, the graph indicated by the reference sign g23 corresponds to the graph g13 in FIG. 5, and illustrates the chronological change in the exposure based on the control by the medical observation device 100 diagrammatically as the chronological change in the detection value corresponding to the exposure.

The example illustrated in FIG. 6 is similar to the example illustrated in FIG. 5, in that the medical observation device 100 starts measuring the counter value of the stable time at the timing T1. On the other hand, as a consideration of the graph g23 demonstrates, the example illustrated in FIG. 6 differs from the example illustrated in FIG. 5, in that the medical observation device 100 does not conduct the exposure control of the imaging section 110 in the interval in which the detection value indicates a value inside the certain range R1, and later starts the exposure control of the imaging section 110 using the timing T3 at which the detection value indicates a value outside the range R1 as a base point.

Note that for the interval from the timing T3, similarly to the example illustrated in FIG. 5, the medical observation device 100 maintains the exposure of the imaging section 110 at the correct exposure corresponding to the reference value L11 in the interval up to the timing T4 at which the counter value of the stable time decreases to reach 0. Additionally, from the timing T4, the medical observation device 100 switches the exposure control of the imaging section 110 to control that follows the detection value. According to such control, in the example illustrated in FIG. 6, in a second interval in which to suppress sudden changes in exposure due to a disturbance (the interval indicated from the timings T1 to T4), the medical observation device 100 maintains the exposure of the imaging section 110 at an exposure based on a detection value inside the certain range R1.

Also, as another example, in the examples illustrated in FIGS. 5 and 6, the medical observation device 100 treats the reference value L11 as a target value to control the operation of the imaging section 110 so that the exposure of the imaging section 110 is maintained at an exposure corresponding to the target value. On the other hand, the target value for controlling the exposure of the imaging section 110 is not necessarily limited to a certain reference value L11.

Figure 7:
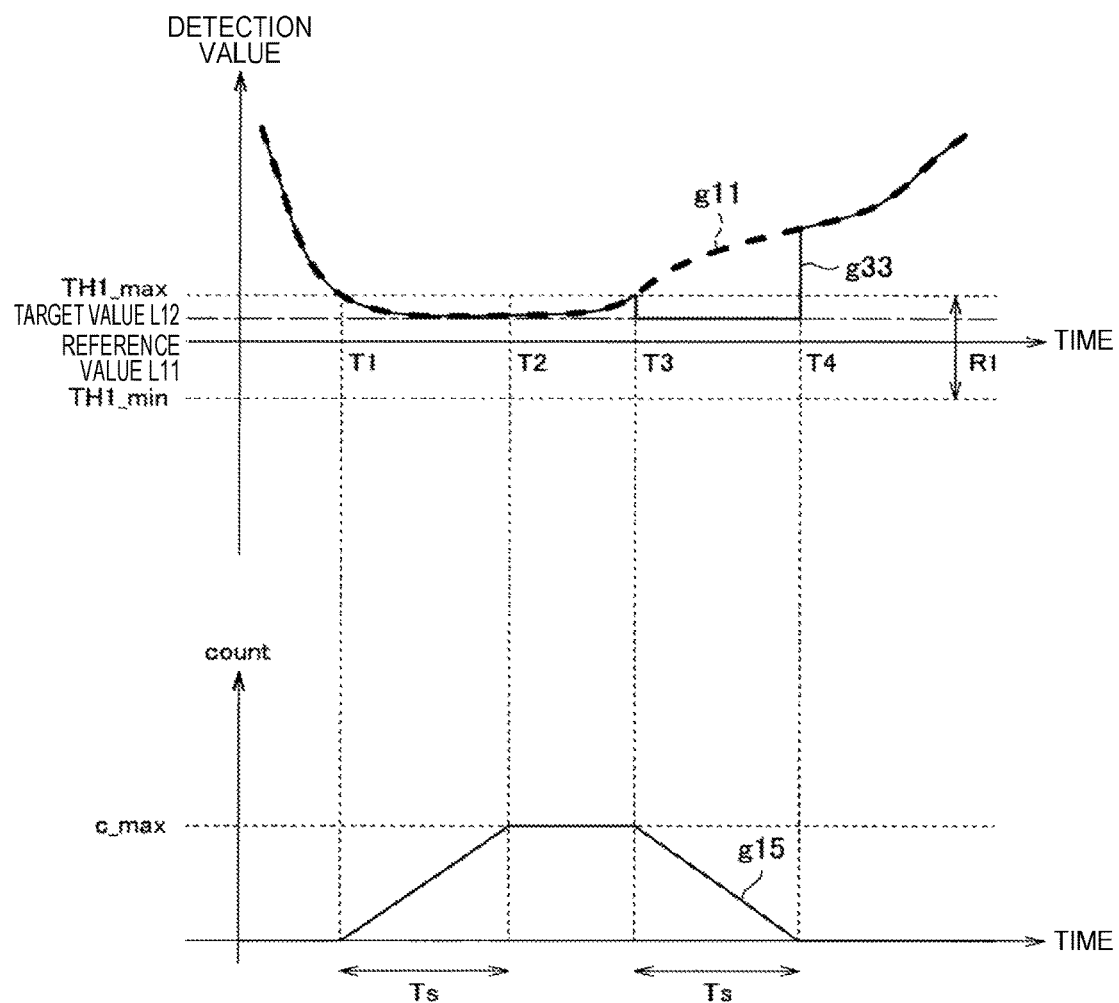
FIG. 7 is an explanatory diagram for explaining another example of exposure control by a medical observation device according to a modification of the embodiment.

For example, FIG. 7 is an explanatory diagram for explaining another example of exposure control by a medical observation device according to a modification of the present embodiment. Also, the vertical axis and the horizontal axis in each of the graphs respectively illustrated on the top and the bottom of FIG. 7 correspond to the vertical axis and the horizontal axis of the graphs respectively illustrated on the top and the bottom of FIG. 6, for example. Note that in the example illustrated in FIG. 7, the graphs indicated by the reference signs g11 and g15 are similar to the graphs g11 and g15 in the example illustrated in FIG. 6, and thus detailed description will be reduced or omitted. Also, the graph indicated by the reference sign g33 corresponds to the graph g23 in FIG. 6, and illustrates the chronological change in the exposure based on the control by the medical observation device 100 diagrammatically as the chronological change in the detection value corresponding to the exposure.

In the example illustrated in FIG. 7, as indicated by the graph g15, the operation related to the measurement of the counter value of the stable time by the medical observation device 100 is similar to the examples illustrated in FIGS. 5 and 6. On the other hand, the example illustrated in FIG. 7 differs from the examples illustrated in FIGS. 5 and 6 in that, as indicated by the graph g33, the medical observation device 100 sets a target value L12 different from the reference value L11 as the target value of the exposure control.

As a specific example, the medical observation device 100 calculates the target value L12 based on statistics of the detection value in an interval in which the acquired detection value indicates a value inside the range R1 (such as an average of the detection value from the timings T1 to T2, or a moving average of the detection value based on a certain time step, for example). Subsequently, from the timing T3 at which the acquired detection value indicates a value outside the range R1, the medical observation device 100 controls the operation of the imaging section 110 so that the exposure of the imaging section 110 is maintained at the exposure corresponding to the calculated target value L12. According to such control, in the example illustrated in FIG. 7, in a second interval in which to suppress sudden changes in exposure due to a disturbance (the interval indicated from the timings T1 to T4), the medical observation device 100 maintains the exposure of the imaging section 110 at an exposure based on a detection value inside the certain range R1.

Next, another example of exposure control by a medical observation device according to a modification of the present embodiment will be described with reference to FIG. 8. The vertical axis and the horizontal axis in each of the graphs respectively illustrated on the top and the bottom of FIG. 8 correspond to the vertical axis and the horizontal axis of the graphs respectively illustrated on the top and the bottom of FIG. 6, for example. In addition, in FIG. 8, the graph indicated by the reference sign g41 represents the chronological change in the detection value acquired based on the detection process by the medical observation device 100 (imaging signal processing section 131). Also, the graph indicated by the reference sign g43 illustrates the chronological change in the exposure based on the control by the medical observation device 100 (exposure control section 135) diagrammatically as the chronological change in the detection value corresponding to the exposure. Also, the graph indicated by the reference sign g45 represents the chronological change in the counter value of the stable time. Also, the range indicated by the reference sign R1 is similar to the examples described with reference to FIGS. 5 to 7.

In the example illustrated in FIG. 8, as illustrated by the graph g41, the acquired detection value indicates a value inside the range R1 in the interval from the timings T21 to T23, and subsequently, temporarily indicates a value outside the range R1 due to a disturbance or the like in the interval from the timings T23 to T24. Also, the acquired detection value indicates a value inside the range R1 in the interval from the timings T24 to T26, and indicates a value outside the range R1 from the timing T26.

At this point, consider the chronological change in the counter value of the stable time illustrated as the graph g45. Since the detection value indicates a value inside the range R1 in the interval from the timings T21 to T22, the counter value of the stable time increases chronologically, and reaches the upper limit c_max at the timing T22. Also, in the interval from the timings T22 to T23, the detection value indicates a value inside the range R1, but the counter value of the stable time has reached the upper limit c_max, and thus is maintained so as not to exceed the upper limit c_max.

Also, in the interval from the timings T23 to T24, since the detection value indicates a value outside the range R1, the counter value of the stable time decreases chronologically. Note that in the example illustrated in FIG. 8, at the timing T24, the detection value indicates a value inside the range R1 again, before the counter value of the stable time reaches 0. For this reason, in the interval from the timings T24 to T25, the counter value of the stable time increases chronologically again, and reaches the upper limit c_max at the timing T25. Also, in the interval from the timings T25 to T26, the detection value indicates a value inside the range R1, but the counter value of the stable time has reached the upper limit c_max, and thus is maintained so as not to exceed the upper limit c_max.

Also, from the timing T26, the detection value indicates a value outside the range R1, and thus the counter value of the stable time decreases chronologically by the amount the counter value increased up to the timing T26, and reaches 0 at the timing T27.

Next, the exposure control of the imaging section 110 by the medical observation device 100 (exposure control section 135) will be described with reference to the graph g43. In the example illustrated in FIG. 8, if the acquired detection value indicates a value outside the range R1, and in addition, the counter value of the stable time indicates a value greater than 0, the medical observation device 100 controls the operation of the imaging section 110 so that the exposure of the imaging section 110 is maintained at the exposure corresponding to the reference value L11.

Figure 8:
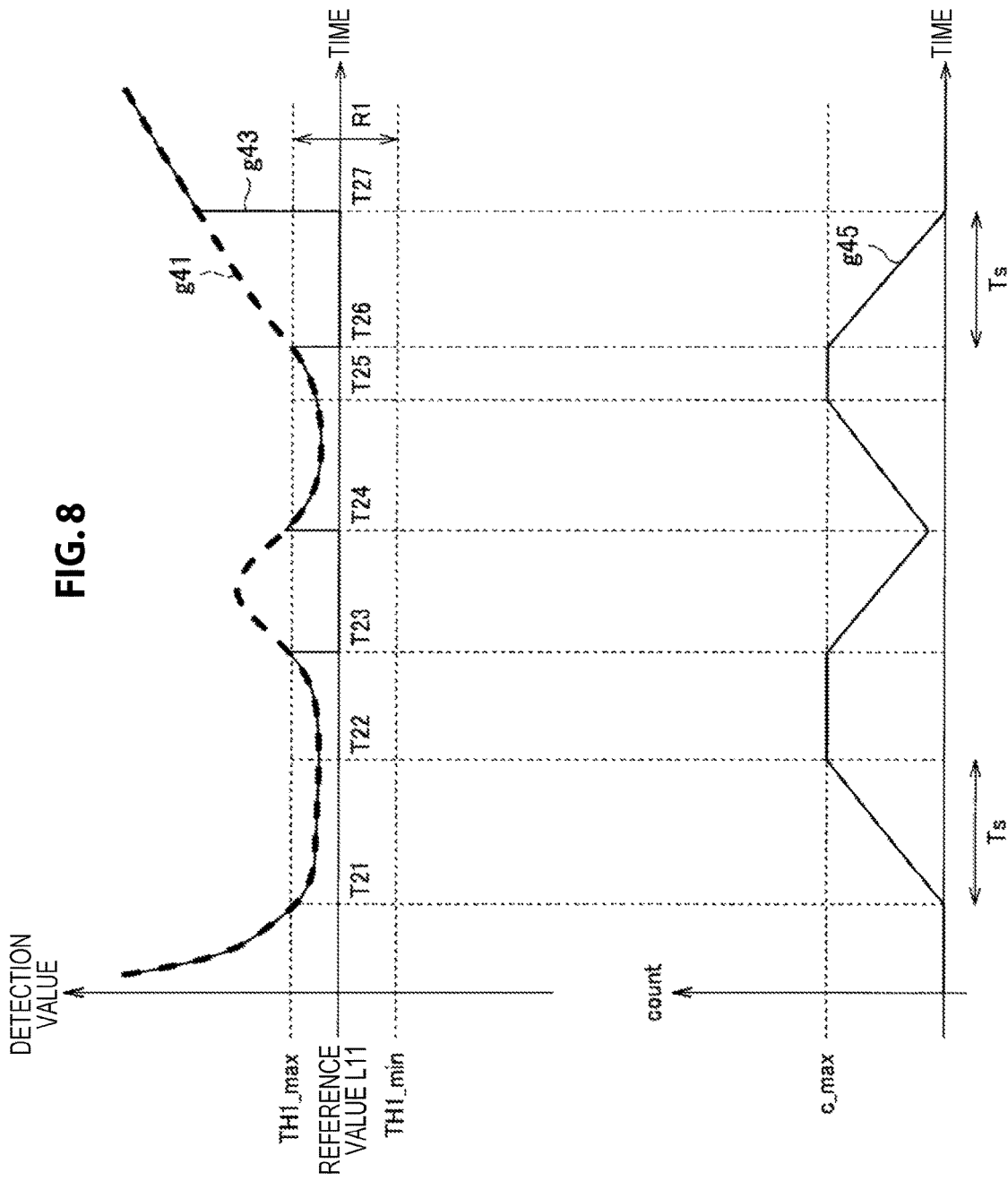
FIG. 8 is an explanatory diagram for explaining another example of exposure control by a medical observation device according to a modification of the embodiment.

For example, in the example illustrated in FIG. 8, in the interval from the timings T23 to T24, the acquired detection value indicates a value outside the range R1, and in addition, the counter value of the stable time indicates a value greater than 0. For this reason, in this interval, the medical observation device 100 controls the operation of the imaging section 110 so that the exposure of the imaging section 110 is maintained at the exposure corresponding to the reference value L11.

Next, consider the interval from the timings T24 to T26. At the timing T24, the acquired detection value indicates a value inside the range R1 again. For this reason, the medical observation device 100 switches the operation of the imaging section 110 so that the exposure of the imaging section 110 follows the acquired detection value.

Also, in the interval from the timing T26, the acquired detection value indicates a value outside the range R1. Additionally, the counter value of the stable time decreases chronologically from the timing T26, and reaches 0 at the timing T27. In other words, in the interval from the timings T26 to T27, the medical observation device 100 controls the operation of the imaging section 110 so that the exposure of the imaging section 110 is maintained at the exposure corresponding to the reference value L11. Subsequently, from the timing T27, the medical observation device 100 switches the operation of the imaging section 110 so that the exposure of the imaging section 110 follows the acquired detection value.

Note that in the example illustrated in FIG. 8, the interval from the timings T21 to T23 and the interval from the timings T24 to T26, in which the acquired detection value indicates a value inside the range R1, correspond to the first interval. Meanwhile, the interval from the timings T21 to T27 corresponds to the second interval in which to suppress sudden changes in exposure due to a disturbance.

As above, in the example illustrated in FIG. 8, if the acquired detection value indicates a value outside the range R1, and in addition, the counter value of the stable time indicates a value greater than 0, the medical observation device 100 controls the operation of the imaging section 110 so that the exposure of the imaging section 110 is maintained at the exposure corresponding to the reference value L11. According to such control, in the example illustrated in FIG. 8, in the interval in which the acquired detection value indicates a value outside the range R1, which takes place during the decided second interval, the medical observation device 100 becomes able to control the operation of the imaging section 110 so that the exposure of the imaging section 110 is maintained at the exposure corresponding to the reference value L11.

Note that the exposure control by the medical observation device 100 described above is merely one example, and the mode of such control is not particularly limited, insofar as the medical observation device is able to maintain the exposure of the imaging section 110 at an exposure based on a detection value inside the certain range R1 in the calculated second interval. For example, in the example illustrated in FIG. 8, in the interval from the timings T21 to T27, the medical observation device 10 may control the operation of the imaging section 110 so that the exposure of the imaging section 110 is maintained at the exposure corresponding to the reference value L11, similarly to the example described with reference to FIG. 5. Also, as another example, the medical observation device 100 may start the exposure control of the imaging section 110 at the timing T23, and maintain the exposure control until the timing T27. In other words, in the interval from the timings T23 to T27, the medical observation device 100 may control the operation of the imaging section 110 so that the exposure of the imaging section 110 is maintained at the exposure corresponding to the reference value L11. Also, in the example illustrated in FIG. 8, the medical observation device 100 may also separately calculate a target value L12 different from the reference value L11, and control the exposure of the imaging section 110 based on the target value L12, similarly to the example illustrated in FIG. 7.

The above thus describes, as a modification of the medical observation device according to the present embodiment, other examples of exposure control by the medical observation device with reference to FIGS. 6 to 8.

<6. Applications>

Figure 9:
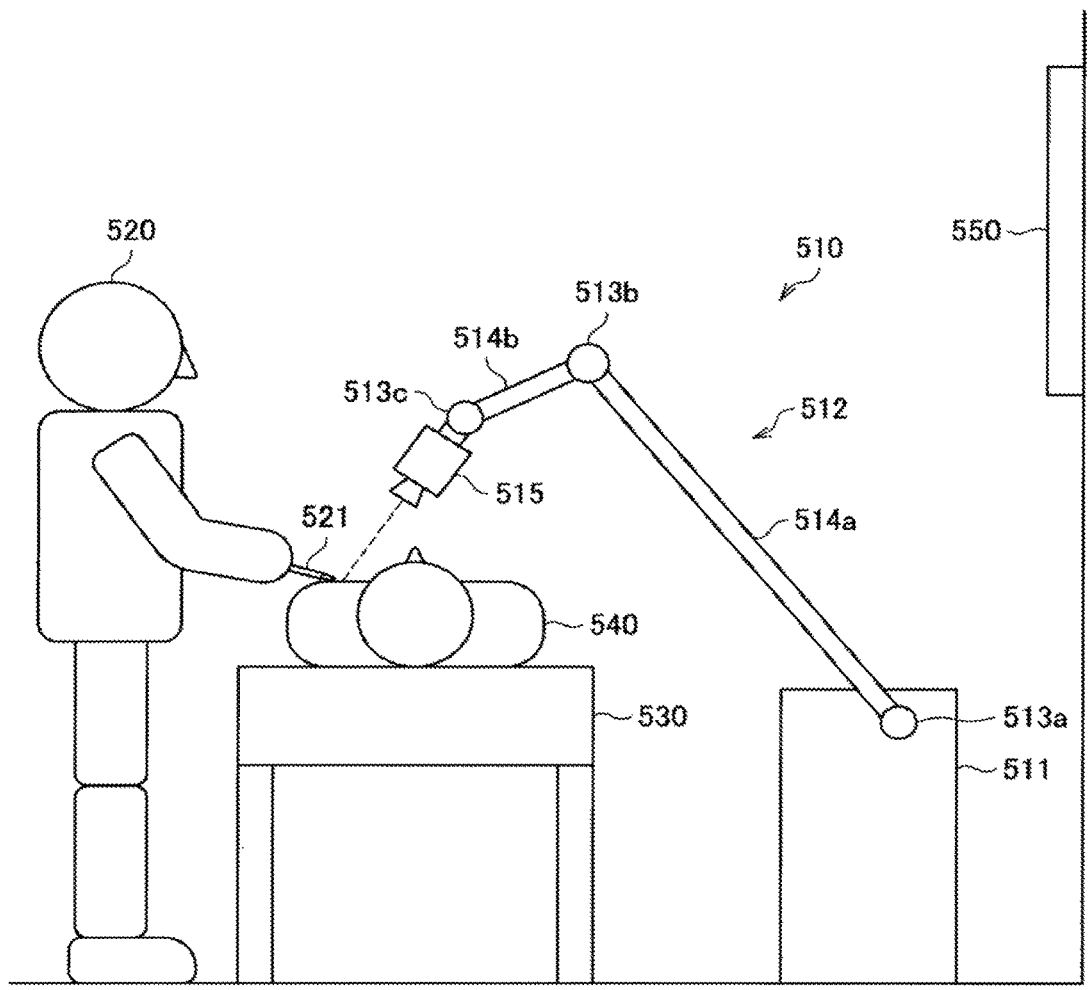
FIG. 9 is an explanatory diagram for explaining an application of a medical observation device according to the embodiment.

Next, FIG. 9 will be referenced to describe an example of a case of using a surgical video microscope device equipped with an arm as another application of a medical observation device according to the present embodiment. FIG. 9 is an explanatory diagram for explaining an application of a medical observation device according to the embodiment.

FIG. 9 diagrammatically illustrates how a medical procedure is performed using a surgical video microscope device. Specifically, referring to FIG. 9, a state is illustrated in which a physician acting as the surgeon (user) 520 is using a surgical tool 521, such as a scalpel, tweezers, or forceps, for example, to perform surgery on a subject (patient) 540 lying on an operating table 530. Note that in the following description, medical procedure is used as a collective term to denote various types of medical treatments performed by a physician acting as the user 520 on a patient acting as the subject 540, such as a surgery or an examination. Also, although the example illustrated in FIG. 9 illustrates a situation of surgery as an example of a medical procedure, the medical procedure in which the surgical video microscope device 510 is used is not limited to surgery, and may be any of various other types of medical procedures.

Beside the operating table 530, the surgical video microscope device 510 according to the present embodiment is provided. The surgical video microscope device 510 is equipped with a base section 511 which acts as a base, an arm section 512 which extends from the base section 511, and an imaging unit 515 connected as a front edge unit on the front edge of the arm section 512. The arm section 512 includes multiple joint sections 513a, 513b, and 513c, multiple links 514a and 514b joined by the joint sections 513a and 513b, and the imaging unit 515 provided on the front edge of the arm section 512. In the example illustrated in FIG. 9, for the sake of simplicity, the arm section 512 includes three joint sections 513a to 513c and two links 514a and 514b, but in actuality, the degrees of freedom in the positions and the orientations of the arm section 512 and the imaging unit 515 may be considered to appropriately configure factors such as the numbers and shapes of the joint sections 513a to 513c and the links 514a and 514b, and the directions of the drive shafts of the joints 513a to 513c, so as to achieve the desired degrees of freedom.

The joint sections 513a to 513c have a function of rotatably joining the links 514a and 514b to each other, and by driving the rotation of the joint sections 513a to 513c, the driving of the arm section 512 is controlled.

On the front edge of the arm section 512, the imaging unit 515 is connected as a front edge unit. The imaging unit 515 is a unit that acquires an image of an imaging target, and is a device such as a camera capable of capturing a moving image or a still image, for example. As illustrated in FIG. 9, the orientations and the positions of the arm section 512 and the imaging unit 515 are controlled by the surgical video microscope device 510 so that the imaging unit 515 provided on the front edge of the arm section 512 captures the operating site of the subject 540. Note that the configuration of the imaging unit 515 connected as the front edge unit on the front edge of the arm section 512 is not particularly limited, and the imaging unit 515 may be configured as an endoscope or a microscope, for example. Additionally, the imaging unit 515 may also be configured to be removable from the arm section 512. According to such a configuration, an imaging unit 515 depending on the usage scenario may be connected appropriately to the front edge of the arm section 512 as the front edge unit, for example. Note that although the description herein focuses on a case in which the imaging unit 515 is applied as the front edge unit, obviously the front edge unit connected to the front edge of the arm section 512 is not necessarily limited to the imaging unit 515.

Also, at a position facing the user 520, a display device 550 such as a monitor or a display is installed. An image of the operating site acquired by the imaging unit 515 is subjected to various types of image processing by an image processing device built into or externally attached to the surgical video microscope device 510, and then displayed on a display screen of the display device 550 as an electronic image. According to such a configuration, the user 520 becomes able to perform various treatments (such as surgery, for example) while looking at an electronic image of the operating site displayed on the display screen of the display device 550.

Note that in the example illustrated in FIG. 9, the imaging unit 515 includes the imaging section 110 discussed earlier with reference to FIG. 3, for example. Also, the imaging processing device that performs various types of image processing on an image of the operating site acquired by the imaging unit 515 corresponds to an example of the control section 130 discussed earlier with reference to FIG. 3. Similarly, the display device 550 corresponds to an example of the display section 150 discussed earlier with reference to FIG. 3.

The above thus references FIG. 9 to describe an example of a case of using a surgical video microscope device equipped with an arm as another application of a medical observation device according to the present embodiment.

<7. Hardware Configuration>

Figure 10:
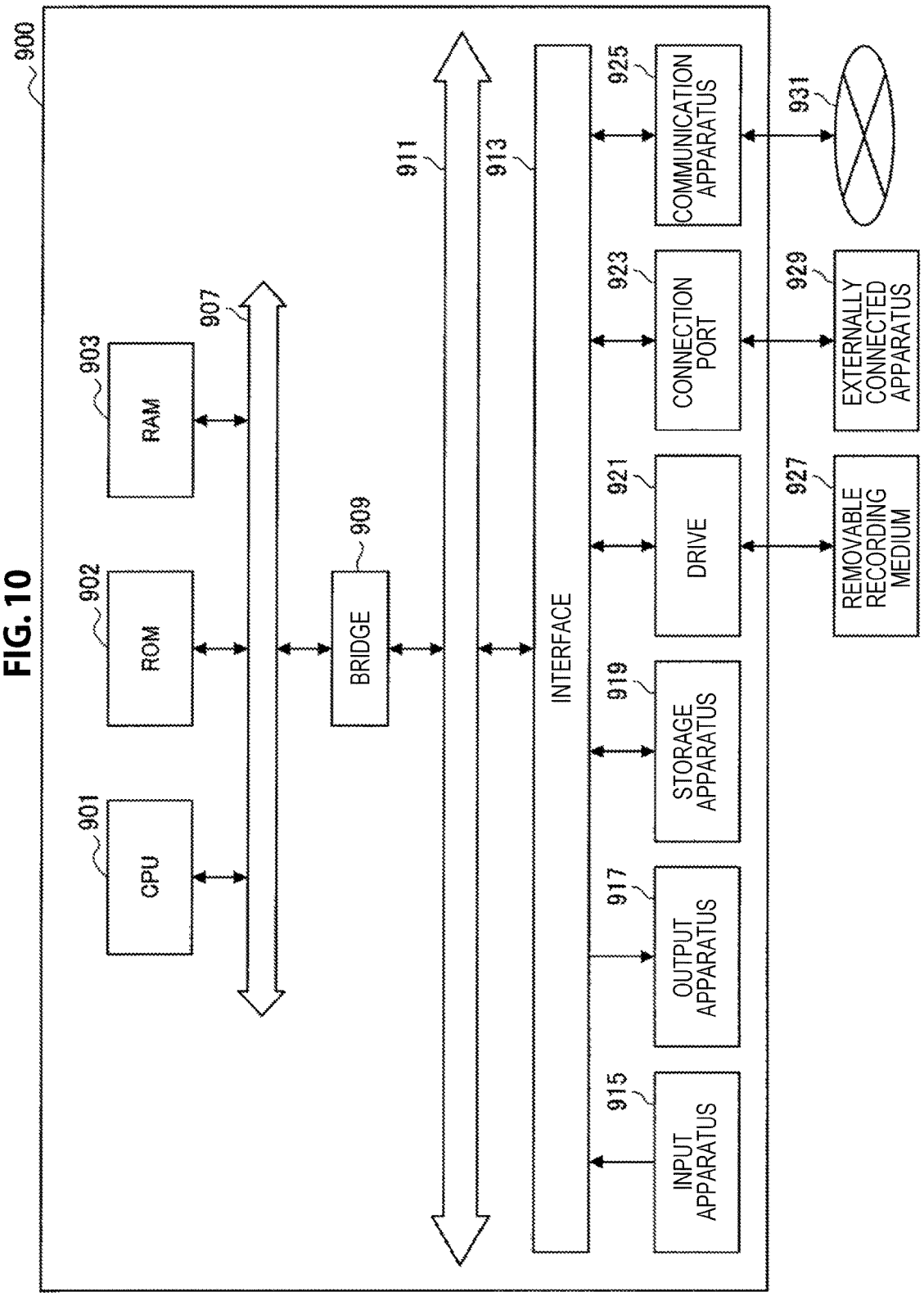
FIG. 10 is a function block diagram illustrating an example configuration of the hardware configuration of an information processing device configured as a medical observation device according to the embodiment.

Next, an example of a hardware configuration of an information processing apparatus 900 configured as a medical observation device according to the present embodiment will be described in detail with reference to FIG. 10. FIG. 10 is a function block diagram illustrating an example configuration of the hardware configuration of an information processing apparatus 900 configured as a medical observation device according to an embodiment of the present disclosure.

As illustrated in FIG. 10, the information processing apparatus 900 mainly includes a CPU 901, a ROM 903, and a RAM 905. Furthermore, the information processing apparatus 900 also includes a host bus 907, a bridge 909, an external bus 911, an interface 913, an input apparatus 915, an output apparatus 917, and a storage apparatus 919. Furthermore, the information processing apparatus 900 also includes a drive 921, a connection port 923, and a communication apparatus 925.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like. Note that the respective components of the control section 130 discussed earlier with reference to FIG. 3 may be realized by the CPU 901, for example.

The host bus 907 is connected to the external bus 911 such as a PCI (Peripheral Component Interconnect/Interface) bus via the bridge 909. Additionally, the input apparatus 915, the output apparatus 917, the storage apparatus 919, the drive 921, the connection port 923, and the communication apparatus 925 are connected to the external bus 911 via the interface 913.

The input apparatus 915 is an operation mechanism operated by a user, such as a mouse, a keyboard, a touch panel, buttons, a switch, a lever, or a pedal. Also, the input apparatus 915 may be a remote control mechanism (a so-called remote control) using, for example, infrared light or other radio waves, or may be an externally connected apparatus 929 such as a mobile phone or a PDA conforming to the operation of the information processing apparatus 900. Furthermore, the input apparatus 915 generates an input signal based on, for example, information which is input by a user with the above operation mechanism, and is configured from an input control circuit for outputting the input signal to the CPU 901. The user of the information processing apparatus 900 can input various data to the information processing apparatus 900 and can instruct the information processing apparatus 900 to perform processing by operating this input apparatus 915.

The output apparatus 917 is configured from a device capable of visually or audibly notifying acquired information to a user. Examples of such device include display apparatuses such as a CRT display apparatus, a liquid crystal display apparatus, a plasma display apparatus, an EL display apparatus and lamps, audio output apparatuses such as a speaker and a headphone, a printer, and the like. For example, the output apparatus 917 outputs a result obtained by various processings performed by the information processing apparatus 900. More specifically, the display apparatus displays, in the form of texts or images, a result obtained by various processes performed by the information processing apparatus 900. On the other hand, the audio output apparatus converts an audio signal such as reproduced audio data and sound data into an analog signal, and outputs the analog signal. Note that the display section 150 discussed earlier with reference to FIG. 3 may be realized by the output apparatus 917, for example.

The storage apparatus 919 is a device for storing data configured as an example of a storage unit of the information processing apparatus 900 and is used to store data. The storage apparatus 919 is configured from, for example, a magnetic storage apparatus such as a HDD (Hard Disk Drive), a semiconductor storage apparatus, an optical storage apparatus, or a magneto-optical storage apparatus. This storage apparatus 919 stores programs to be executed by the CPU 901, and various data.

The drive 921 is a reader/writer for recording medium, and is embedded in the information processing apparatus 900 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (a registered trademark) medium. The removable recording medium 927 may be a CompactFlash (CF; a registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing apparatuses to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the externally connected apparatus 929 connecting to this connection port 923, the information processing apparatus 900 directly obtains various data from the externally connected apparatus 929 and provides various data to the externally connected apparatus 929.

The communication apparatus 925 is a communication interface configured from, for example, a communication apparatus for connecting to a communication network 931. The communication apparatus 925 is, for example, a wired or wireless LAN (Local Area Network), Bluetooth (registered trademark), a communication card for WUSB (Wireless USB), or the like. Alternatively, the communication apparatus 925 may be a router for optical communication, a router for ADSL (Asymmetric Digital Subscriber Line), a modem for various communications, or the like. This communication apparatus 925 can transmit and receive signals and the like in accordance with a predetermined protocol such as TCP/IP on the Internet and with other communication apparatuses, for example. The communication network 931 connected to the communication apparatus 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 900 constituting a medical stereoscopic observation system according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment. Although not shown in FIG. 10, for example, it naturally includes various configurations corresponding to the medical stereoscopic observation device described above.

Note that it is also possible to develop a computer program for realizing the respective functions of the information processing apparatus 900 constituting a medical stereoscopic observation system according to the present embodiment as discussed above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium.

<8. Conclusion>

Thus, as described above, a medical observation device according to the present embodiment, in the case of recognizing that the detection value indicates a value within a certain range, measures a first interval in which the detection value indicates a value inside the range, and based on the measurement result of the first interval, decides a second interval in which to suppress sudden changes in exposure due to a disturbance. Subsequently, even if the detection value changes suddenly due to a disturbance or the like during the decided second interval, the medical observation device controls the operation of the imaging section so that the exposure of the imaging section is maintained at an exposure corresponding to a detection value within the certain range (for example, the correct exposure corresponding to the reference value).

According to such control, even when the detection value changes suddenly due to a disturbance, like a high-luminance subject such as forceps or gauze entering into the observation range, the medical observation device according to the present embodiment maintains the exposure of the imaging section, and suppresses sudden changes of brightness in the image of the subject (image of the target of observation), such as an affected area. In other words, according to the medical observation device according to the present embodiment, even if a high-luminance object such as forceps or gauze temporarily enters into the observation range, it becomes possible to suppress the occurrence of a situation in which the captured image of the target of observation becomes dark.

Also, as discussed earlier, the second interval in which a medical observation device according to the present embodiment suppresses sudden changes in exposure due to a disturbance is decided based on the first interval in which the detection value indicates a value inside the certain range. Namely, the medical observation device controls the second interval to be longer as the first interval becomes longer. In other words, the medical observation device according to the present embodiment dynamically controls the interval in which the exposure of the imaging section is maintained at an exposure corresponding to a detection value inside the certain range (for example, the correct exposure), according to changes of brightness in the observation range. For this reason, according to the medical observation device according to the present embodiment, it becomes possible to achieve, with a more favorable mode, both the suppression of sudden changes of brightness in the image of the subject as discussed above, and the tracking of the brightness of the image with respect to changes of brightness in the observation range.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)

A medical observation device, including:

an acquisition section that acquires a sensing result of a brightness of an image of a subject in a living organism; and a control section that decides, according to a first interval in which the brightness sensing result indicates a value inside a certain range, a second interval in which to maintain an exposure of an imaging section at an exposure corresponding to a value included in the range.

(2)

The medical observation device according to (1), wherein the control section decides, according to the first interval using as a base point a timing at which the value inside the range is sensed as the sensing result, the second interval using the timing as a base point.

(3)

The medical observation device according to (2), wherein the control section starts control of the exposure of the imaging section, using the timing as a base point.

(4)

The medical observation device according to (2), wherein the control section starts control of the exposure of the imaging section, using another timing later than the timing during the second interval as a base point.

(5)

The medical observation device according to (4), wherein the other timing is a timing at which a value outside the range is sensed as the sensing result.

(6)

The medical observation device according to (2), wherein the control section controls the exposure of the imaging section in an interval in which the sensing result indicates a value outside the range during the second interval.

(7)

The medical observation device according to any one of (1) to (6), wherein the control section controls the imaging section so that the exposure of the imaging section is maintained at an exposure corresponding to a certain target value included in the range.

(8)

The medical observation device according to any one of (1) to (6), wherein the control section calculates a target value for controlling the exposure of the imaging section based on the sensing result.

(9)

The medical observation device according to any one of (1) to (8), wherein
the control section sets an increase of the second interval according to the first interval, in a range that does not exceed a certain threshold value.

(10)

The medical observation device according to any one of (1) to (9), further including:
the imaging section.

(11)

The medical observation device according to (10), wherein
the imaging section is an endoscope configured to be inserted into a body cavity of a patient.

(12)

The medical observation device according to (10), wherein
the imaging section is a microscope section including an optical system that acquires an optical image of the subject, and
the medical observation device further includes a support section that supports the microscope section.

(13)

A medical observation method, executed by a processor, including:
acquiring a sensing result of a brightness of an image of a subject in a living organism; and
deciding, according to a first interval in which the brightness sensing result indicates a value inside a certain range, a second interval in which to maintain an exposure of an imaging section at an exposure corresponding to a value included in the range.

REFERENCE SIGNS LIST 1 endoscopic surgical system
11 camera head
11 endoscope
13 CCU
15 display device
17 light source device
21 treatment tool device
22 energy treatment tool
23 forceps
24 pneumoperitoneum device
25a, 25b trocar
26 recorder
27 printer
31 cart
33 patient bed
35 footswitch
100 medical observation device
110 imaging section
111 imaging optical system
113 image sensor
130 control section
131 imaging signal processing section
133 image processing section
135 exposure control section
150 display section

The invention claimed is:
1. A medical observation device, comprising: circuitry configured to
acquire a sensing result of a brightness of an image of a subject in a living organism, and
decide, according to a first time interval in which the brightness sensing result indicates a value inside a certain range, a second time interval in which to maintain an exposure of an imaging device at an exposure corresponding to a value included in the range, and
instruct maintaining of the exposure of the imaging device at the exposure corresponding to the value included in the range based on the decided second time interval,
wherein the circuitry is further configured to decide, according to the first time interval using as a base point a timing at which the value inside the range is sensed as the sensing result, the second time interval based on the timing.

2. The medical observation device according to claim 1, wherein the circuitry is further configured to start control of the exposure of the imaging device, using the timing as a base point.

3. The medical observation device according to claim 1, wherein the circuitry is further configured to start control of the exposure of the imaging device, using another timing later than the timing during the second time interval as a base point.

4. The medical observation device according to claim 3, wherein the other timing is a timing at which a value outside the range is sensed as the sensing result.

5. The medical observation device according to claim 1, wherein the circuitry is further configured to control the exposure of the imaging device in a time interval in which the sensing result indicates a value outside the range during the second time interval.

6. The medical observation device according to claim 1, wherein the circuitry is further configured to control the imaging device so that the exposure of the imaging device is maintained at an exposure corresponding to a certain target value included in the range.

7. The medical observation device according to claim 1, wherein the circuitry is further configured to calculate a target value for controlling the exposure of the imaging device based on the sensing result.

8. The medical observation device according to claim 1, wherein the circuitry is further configured to set an increase of the second time interval according to the first time interval, in a range that does not exceed a certain threshold value.

9. The medical observation device according to claim 1, further comprising:
the imaging device.

10. The medical observation device according to claim 9, wherein
the imaging device is an endoscope configured to be inserted into a body cavity of a patient.

11. The medical observation device according to claim 9, wherein
the imaging device is a microscope including an optical system that acquires an optical image of the subject, and
the medical observation device further comprises a support that supports the microscope.

12. A medical observation method, executed by a processor, comprising:
acquiring a sensing result of a brightness of an image of a subject in a living organism;
deciding, according to a first time interval in which the brightness sensing result indicates a value inside a certain range, a second time interval in which to maintain an exposure of an imaging device at an exposure corresponding to a value included in the range; and instructing maintaining of the exposure of the imaging device at the exposure corresponding to the value included in the range based on the decided second time interval, wherein the deciding further includes deciding, according to the first time interval using as a base point a timing at which the value inside the range is sensed as the sensing result, the second time interval based on the timing.

* * * * *

UNITED STATES PATENT AND TRADEMARK OFFICE
CERTIFICATE OF CORRECTION

PATENT NO. : 10,028,647 B2
APPLICATION NO. : 15/323742
DATED : July 24, 2018
INVENTOR(S) : Masashi Murakita et al.

Page 1 of 1

It is certified that error appears in the above-identified patent and that said Letters Patent is hereby corrected as shown below:

On the Title Page

Item (73), the Assignee's information has been listed incorrectly. Item (73) should read:
-- (73) Assignees: SONY CORPORATION, Tokyo (JP);
        SONY OLYMPUS MEDICAL
        SOLUTIONS INC., Hachioji-shi (JP) --

Signed and Sealed this
Fourth Day of June, 2019

Andrei Iancu
*Director of the United States Patent and Trademark Office*